(12) United States Patent
Ohyu (10) Patent No.: US 11,664,127 B2
(45) Date of Patent: May 30, 2023

(54) MEDICAL INFORMATION PROCESSING APPARATUS, MEDICAL INFORMATION PROCESSING METHOD, AND ELECTRONIC MEDICAL RECORD SYSTEM

(71) Applicant: Canon Medical Systems Corporation, Otawara (JP)

(72) Inventor: Shigeharu Ohyu, Yaita (JP)

(73) Assignee: Canon Medical Systems Corporation, Otawara (JP)

( * ) Notice: Subject to any disclaimer, the term of this patent is extended or adjusted under 35 U.S.C. 154(b) by 264 days.

(21) Appl. No.: 16/937,812

(22) Filed: Jul. 24, 2020

(65) Prior Publication Data

US 2021/0035688 A1 Feb. 4, 2021

(30) Foreign Application Priority Data

Aug. 2, 2019 (JP) .............................. JP2019-143034

(51) Int. Cl.
| | |
|---|---|
| *G16H 50/30* | (2018.01) |
| *G16H 50/20* | (2018.01) |
| *G16H 50/50* | (2018.01) |
| *G06F 3/14* | (2006.01) |
| *G16H 15/00* | (2018.01) |
| *G06Q 10/02* | (2012.01) |
| *G16H 10/60* | (2018.01) |
| *G16H 40/20* | (2018.01) |

(52) U.S. Cl.
CPC .............. *G16H 50/20* (2018.01); *G06F 3/14* (2013.01); *G06Q 10/02* (2013.01); *G16H 10/60* (2018.01); *G16H 15/00* (2018.01); *G16H 40/20* (2018.01); *G16H 50/30* (2018.01); *G16H 50/50* (2018.01)

(58) Field of Classification Search
None
See application file for complete search history.

(56) References Cited

U.S. PATENT DOCUMENTS

| | | | | |
|---|---|---|---|---|
| 2005/0015002 | A1* | 1/2005 | Dixon | .................. A61B 5/1038 600/595 |
| 2005/0149352 | A1* | 7/2005 | Grasso | .................. G16H 70/20 705/2 |
| 2005/0222868 | A1* | 10/2005 | Kantrowitz | ............ G16H 40/20 705/2 |
| 2005/0228697 | A1* | 10/2005 | Funahashi | .............. G16H 40/20 705/2 |
| 2007/0265882 | A1* | 11/2007 | Jennings | ............ G06Q 10/1095 705/7.19 |
| 2020/0402627 | A1* | 12/2020 | Rosomoff | .......... G06Q 10/1097 |

FOREIGN PATENT DOCUMENTS

| | | |
|---|---|---|
| JP | 2012-088986 A | 5/2012 |
| JP | 2012-139411 A | 7/2012 |
| JP | 2012-143275 A | 8/2012 |

\* cited by examiner

*Primary Examiner* — Robert A Sorey
(74) *Attorney, Agent, or Firm* — Oblon, McClelland, Maier & Neustadt, L.L.P.

(57) ABSTRACT

According to one embodiment, a medical information processing apparatus includes processing circuitry. The processing circuitry predicts, based on subject information and a prediction model of a disease onset risk, a time course of the disease onset risk in relation to a subject. The processing circuitry presents, based on the time course of the disease onset risk, a recommended period appropriate for arranging a next examination or medical procedure.

15 Claims, 6 Drawing Sheets

MEDICAL INFORMATION PROCESSING APPARATUS, MEDICAL INFORMATION PROCESSING METHOD, AND ELECTRONIC MEDICAL RECORD SYSTEM

CROSS-REFERENCE TO RELATED APPLICATIONS

This application is based upon and claims the benefit of priority from the prior Japanese Patent Application No. 2019-143034, filed Aug. 2, 2019, the entire contents of which are incorporated herein by reference.

FIELD

Embodiments described herein relate generally to a medical information processing apparatus, a medical information processing method, and an electronic medical record system.

BACKGROUND

A risk calculation method to calculate a lifetime risk of having a disease is provided by constructing a model based on an examination result and risk information, such as medical history, of a patient. In this model, a disease onset risk during a certain period or in a lifetime can be predicted based on various risk factors.

Furthermore, a method to calculate and present the next examination period of a patient based on a measurement value obtained by a medical measuring apparatus, such as a bone mineral density measuring apparatus, and a risk factor is provided. However, none of the methods are able to evaluate the time variation of the validity of the examination or the time variation of the magnitude of the risk. Therefore, the next desirable examination period cannot be determined in consideration of those time variations.

DETAILED DESCRIPTION

In general, according to one embodiment, a medical information processing apparatus includes processing circuitry. The processing circuitry predicts, based on subject information and a prediction model of a disease onset risk, a time course of the disease onset risk in relation to a subject. The processing circuitry presents, based on the time course of the disease onset risk, a recommended period appropriate for arranging a next examination or medical procedure.

Hereinafter, a medical information processing apparatus, a medical information processing method, and an electronic medical record system according to the embodiments will be described with reference to the accompanying drawings. In the following embodiments, elements assigned with the same reference numerals perform the same operations, and redundant descriptions will be omitted as appropriate. Hereinafter, an embodiment will be described with reference to the drawings.

First Embodiment

Figure 1:
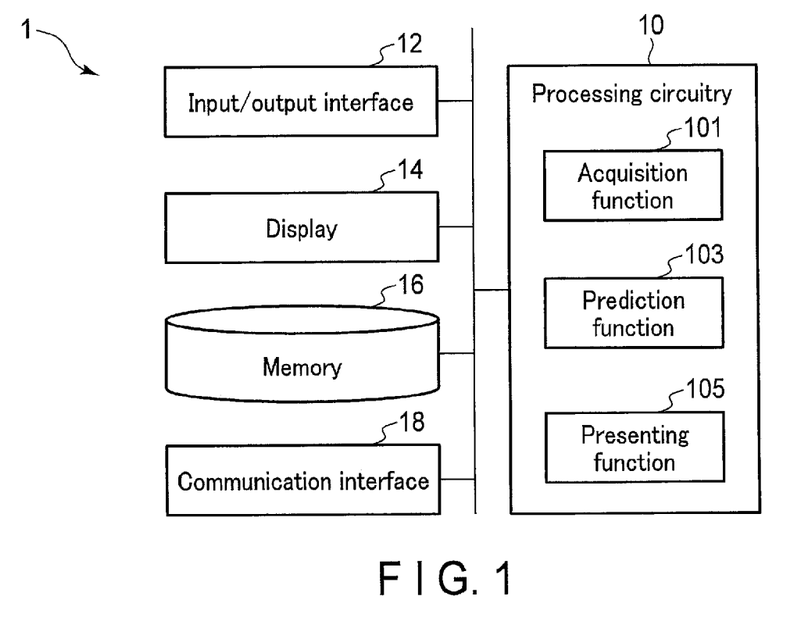
FIG. 1 is a conceptual diagram showing an electronic medical record system according to a first embodiment.

An electronic medical record system according to a first embodiment will be described with reference to FIG. 1.

An electronic medical record system 1 according to the first embodiment includes processing circuitry 10, an input and output interface 12, a display 14, a memory 16, and a communication interface 18.

The electronic medical record system 1 is a system for managing electronic medical records. The electronic medical records are medical care records created by doctors for each patient. Information recorded in the electronic medical records includes subject information on subjects (for example, patients) and medical care information that is generated when medical care is provided to the subjects. The medical care information is managed on, for example, a subject-by-subject basis. The subject information contains information on the subject's race, gender, age group, history of illness, the name of a disease from which the subject is suffering, drugs concurrently used, contraindications, and allergies, etc. The medical care information contains values representing vital signs such as the body temperature, the pulse rate, the blood pressure, and the respiratory rate of each subject.

The input and output interface 12 is an apparatus for medical professionals such as doctors, nurses, and pharmacists to check and input the progress of medical care. The input and output interface 12 is realized by, for example, a mouse, a keyboard, or a touch panel to which an instruction is input by touching an operation surface. An output destination of the input and output interface 12 is, for example, a display 14 and a printing device. The printing device is, for example, a printer, and prints image data which is a printing target on a predetermined sheet of paper. The output destination of the input and output interface 12 is not necessarily equipped with physical output components such as a display device and a printing device, and may be circuitry for transmitting image data to an external output device provided separately from the input and output interface 12.

As the display 14, for example, a CRT display, a liquid crystal display, an organic EL display, an LED display, a plasma display, or any other display known in the relevant technical field may be used as appropriate. The display 14 receives image data for display from the processing circuitry 10, and displays the data in a display format as shown in, for example, FIG. 3 and the drawings thereafter.

The memory 16 is a storage apparatus such as a hard disk drive (HDD), a solid state drive (SSD), an integrated circuitry storage apparatus, or the like that stores various types of information. The memory 16 may not only be the HDD, the SSD, or the like, but may also be a driver that writes and reads various types of information in and from a portable storage medium such as a compact disc (CD), a digital versatile disc (DVD), or a flash memory, or a semiconductor memory element such as a random access memory (RAM). The storage area of the memory 16 may be in the electronic medical record system 1, or in an external storage apparatus connected via a network. The memory 16 may store, for example, risk data and examination result data, prediction data, and data relating to the prediction data, which will be described later.

The communication interface 18 performs communication with other apparatuses via an in-hospital network. For example, image data is acquired from an image server, and the image data is displayed on the display 14.

The processing circuitry 10 includes an acquisition function 101, a prediction function 103, and a presenting function 105.

The acquisition function 101 acquires the risk data and the examination result data via the communication interface 18. The risk data and the examination result data may be collectively referred to as the subject information.

The prediction function 103 predicts a disease onset risk time course in relation to a subject based on the subject information and a prediction model of a disease onset risk.

The presenting function 105 presents a recommended period for the next examination or medical procedure based on the time-depending change of the disease onset risk. The presenting function 105 also presents a period or a point in time assumed to be too early for the next examination or medical procedure (also referred to as a first non-recommended period), which is earlier than the recommended period appropriate for the next examination or medical procedure. The presenting function 105 presents a period or a point in time assumed to be too late for the next examination or medical procedure (also referred to as a second non-recommended period), which is later than the recommended period.

Figure 2:
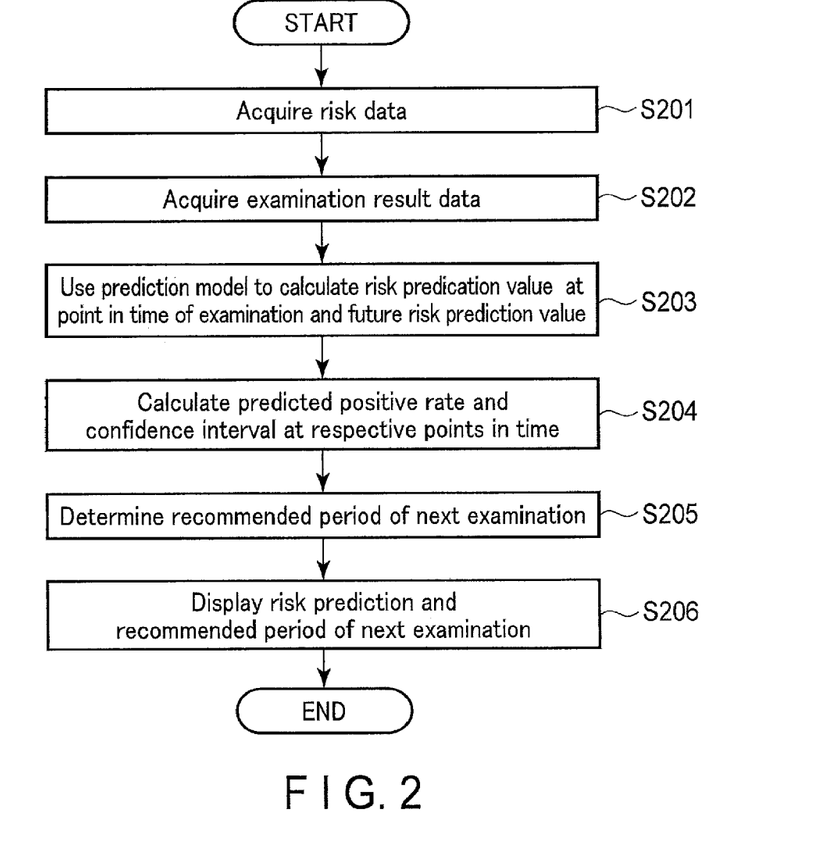
FIG. 2 is a flowchart showing recommended period presentation processing of the electronic medical record system according to the first embodiment.

Recommended period presentation processing of the electronic medical record system 1 according to the first embodiment will now be described with reference to a flowchart of FIG. 2. The first embodiment assumes a case in which, when there is an instruction from a medical record reviewer (a medical professional such as a doctor, hereinafter referred to simply as a user) to present a recommended period on the electronic medical record system 1, the recommended period presentation processing is executed, and the recommended period is presented to the user. It should be noted that the recommended period is not limited to being presented to the medical professional, but may also be presented to the subject.

In step S201, the processing circuitry 10 acquires risk data by the acquisition function 101. The risk data is data relating with the possibility of a disease development associated with a specific case. In the case of, for example, a lung cancer, the risk data may include the presence of medical history of lung cancer, the age of starting smoking, the number of years of smoking, the number of cigarettes smoked per day, and the occupational history relating with asbestos, etc. Furthermore, risk factors such as race, gender and age may also be managed as risk data.

For example, the risk data may be acquired from an external apparatus storing the risk data via the communication interface 18, or may be acquired from the memory 16 in a case where the risk data is stored in the memory 16 of the electronic medical record system 1.

The risk data may also be edited by an operator via an input unit that inputs and changes the risk factor for each subject. The edited risk data may be stored in, for example, the memory 16 together with a subject ID, or may be acquired via the communication interface 18 together with the subject ID.

In step S202, by the acquisition function 101, the processing circuitry 10 acquires examination result data from outside via the communication interface 18. In the case where the examination result data is stored in the memory 16, the processing circuitry 10 acquires the examination result data from the memory 16 by the acquisition function 101. In contrast to image data that is obtained from an examination such as an ultrasound examination, computed tomography (CT) examination, and magnetic resonance imaging (MRI) examination implemented by using a medical image diagnostic apparatus, the examination result data is generated by implementing disease detection processing or determination processing. Specifically, the examination result data includes classification as to whether the examination result by the disease detection processing or the determination processing is positive or negative. The examination result data includes information relating to an examination type, a subject ID, and an examination day, and is stored in the memory 16. The classification may be the two types of positive or negative, or may further be classified into a plurality of types. Furthermore, for example, it may be classified into six classes, in which classes "0, 1, 2, 3" are determined as negative, and classes "4, 5" are determined as positive.

The examination data may include a plurality of pieces of numeric value information correlated to a determination result after preforming publicly known image analysis processing. An example of the image analysis processing is a dynamic analysis model, in which a plurality of indicators relating to tissue perfusion referred to as Ktrans, Vp, and Ve, etc. are calculated as maps, and statistics on a segmentation area of a target tissue, or an average value within a disease candidate area of the segmentation area and standard deviation, etc., are calculated. The calculated statistics are stored in an examination result DB together with data on the examination type, the subject ID, and the examination day.

It should be noted that the classification is not limited to being calculated by the disease detection processing or the determination processing, and may be performed by an image reading specialist classifying the class into the two classes of benign and malignant, or into six classes from 0 to 5. The classification result may be stored in the memory 16 as the examination result data.

Furthermore, examination data obtained originally as the numeric value information, such as a blood test, may be stored in the memory 16 as the examination result data. Alternatively, a value obtained by applying threshold processing to the numeric value information so as to obtain, for example, binary information may be stored in the memory 16 as the examination result data.

In step S203, by the prediction function 103, the processing circuitry 10 executes risk prediction processing which calculates, from the risk data and the examination result data, a risk prediction value at a point in time of examination and risk prediction values at respective points in time in the future by using the prediction model. In other words, the risk prediction values at the point in time of examination and at each point in time in the future are the disease onset risks indicating the possibility of a tissue examination being positive at a point in time of examination and at each point in time in the future. "Onset" is defined as a disease observed and diagnosed as malignant in an examination (for example, a tissue examination) that is considered to have higher accuracy than the standard examination. Regardless of the observation, it does not necessarily indicate that a new malignant disease has appeared.

For example, the risk prediction processing may be triggered by a user selecting "item relating to risk prediction processing" in the items of the examination result displayed on a viewing screen of an electronic medical record.

Here, as an example, the prediction model is a set of discrete number of cases at a point in time of the examination and each point in time of the future. The prediction model may be stored in an electronic medical record system connected to the electronic medical record system 1 or may be stored in the memory 16. The prediction model does not necessarily have to be stored in an independent table, and may be described directly as a computer program in a program format.

Here, an example of the risk prediction processing performed by the prediction function 103 is described in detail.

The risk prediction value calculated by the risk prediction processing is probabilities of the presence of an actual disease at the points in time of the examinations. Even in a case where the actual disease is present, a case in which the examination is determined to be negative and a case in which the examination is determined to be positive will both exist. The probability of the disease should be considered both for the cases of the disease being determined as negative by the examination and actually disease exists, and the cases of the disease being determined as positive by the examination and actually being non-disease.

The risk prediction processing at the point in time of the examination may be calculated by using, for example, an example of a two-by-two contingency table of table 1.

TABLE 1

Two-by-two contingency table

| | Threshold value | Disease | Non-disease | Total |
|---|---|---|---|---|
| Examination positive(Classes 4 to 5) | v1 ≥ t1 | a(0) | b(0) | r1(0) = a(0) + b(0) |
| Examination negative(Classes 0 to 5) | v1 < t1 | c(0) | d(0) | r2(0) = c(0) + d(0) |
| Total | | c1(0) = a(0) + c(0) | c2(0) = b(0) + d(0) | |

In table 1, a, b, c, and d (for convenience of explanation, "(0)" will be omitted) are the number of subjects obtained from the past examination data. Items "examination positive" and "examination negative" in each line of table 1 are examination results of a target examination for performing the risk prediction processing. Items "disease" and "non-disease" in each row are another examination results that are considered to have a higher accuracy than the target examination, such as the histological examination.

Since each value of a, b, c, and d corresponds to the number of corresponding cases counted in past examinations, the value is an integer equal to or larger than zero. On the other hand, when estimated from the risk data using a statistical model such as a Gail model, each of values a, b, c, and d is a real number equal to or larger than zero, and would not be limited to an integer.

For risk prediction at a point in time of the examination for a disease onset risk, a(0), b(0), c(0), and d(0) of the two-by-two contingency table as in table 1, which is prepared from the cases where the months between examination and diagnosis is small, should be used.

"(0)" indicates data that is considered to be x=0 when the number of months from the examination date to the day that diagnosis was made is assumed to be x months (x is a positive number). Here, "diagnosis" indicates an examination result of another type of examination considered to have a higher accuracy than the target examination under consideration. The diagnosis data is, for example, a result of the histological examination. It should be noted that, since a result of histological examination is not always available, instead of the result of the histological examination, "non-disease" diagnosis can be obtained from other type of examination results or a plurality of examination results that include the targeted examination.

For example, when no abnormality can be found from an MRI examination, it may be determined as "non-disease" at the point in time of the MRI examination. Alternatively, in a case where no significant changes are found or only changes indicating improvement are found from CT examinations performed twice or three times with certain interval, it may be determined to be "non-disease".

When the examination result is negative, the probability of the result actually being positive is calculated by 1−NPV based on the contingency table of table 1. Here, "NPV" is a negative predictive value. Therefore, the risk prediction value when the examination result is negative can be calculated from risk prediction value as predicted positive rate=(1−NPV)=c/r2.

On the other hand, when the examination result is positive based on the examination result data, the probability of the result actually being positive is calculated by PPV. Here, "PPV" is a positive predictive value. Therefore, the risk prediction value when the examination result is positive is calculated from risk prediction value as predicted positive rate=(PPV)=a/r1.

That is, the probability of the disease, "predicted positive rate", is calculated by "1−NPV" when the examination result is negative, and by "PPV" when the examination result is positive.

In step S204, by the prediction function 103, the processing circuitry 10 calculates an expected value of the predicted positive rate and a confidence interval of the predicted positive rate as the disease onset risk. The confidence interval indicates a statistical confidence interval for the predicted positive rate. As an example of a calculation method of the confidence interval, there is a calculation method in which c is assumed as a normal distribution.

When the number of samples is assumed as n=r2=c+d, and a success rate is assumed as p=c/r2, if n is large, the distribution of the predicted positive rate is approximated by a normal distribution in which an expected value is p=c/r2, and dispersion is $\sigma^2=p(1-p)=(c/r2)(1-c/r2)$. Accordingly, a 95% confidence interval of the predicted positive rate can be calculated as p±1.96σ.

That is, the expected value of the predicted positive rate can be expressed by equation (1), a lower limit value of the confidence interval of the predicted positive rate can be expressed by equation (2), and an upper limit value of the confidence interval of the predicted positive rate can be expressed by equation (3). It should be noted that these equations are for cases in which the examination result is negative; therefore, in the case where the examination is positive, c and d in the following equations are substituted with a and b respectively.

$$P_{ex}(x) = \frac{c}{c+d} \quad (1)$$

-continued $$P_{lower}(x) = \frac{c}{c+d} - 1.96\sqrt{\frac{c}{(c+d)^2}\left(1 - \frac{c}{c+d}\right)} \quad (2)$$

$$P_{upper}(x) = \frac{c}{c+d} + 1.96\sqrt{\frac{c}{(c+d)^2}\left(1 - \frac{c}{c+d}\right)} \quad (3)$$

As another example of a calculation method of the confidence interval, a binomial distribution is used.

For the calculation method using the binomial distribution of the confidence interval of the predicted positive rate, an incomplete beta function and a calculation of an inverse function thereof are used. Since a general calculating means for the incomplete beta function and the calculation of the inverse function thereof is used, here, explanations thereof are omitted.

In the case of using the binomial distribution, the expected value of the predicted positive rate can be expressed by equation (4), a lower limit value of the confidence interval of the predicted positive rate can be expressed by equation (5), and an upper limit value of the confidence interval of the predicted positive rate can be expressed by equation (6). In the case where the examination is positive, c and d in the following equations are replaced with a and b respectively. Equations are $$P_{ex}(x) = \frac{c}{c+d}, \quad (4)$$

$$P_{lower}(x) = \frac{v_2}{v_2 + v_1 F_{1-\alpha}(v_1, v_2)}, \quad (5)$$
$$v_1 = 2(n - n_{FN} + 1), v_2 = 2n_{FN} \ n = n_{TN} + n_{FN},$$

$$P_{upper}(x) = \frac{v_1 F_{1-\alpha}(v_1, v_2)}{v_2 + v_1 F_{1-\alpha}(v_1, v_2)}, \quad (6)$$
$$v_1 = 2(n_{FN} + 1), v_1 = 2(n - n_{FN}), n = n_{TN} + n_{FN},$$

where $n_{TN}$ is the number of true negatives d in table 1, and $n_{FN}$ is the number of false negatives c in table 1. Furthermore, $F_{1-\alpha}(u_1, u_2)$ denotes an upper side F value corresponding with a significance level $\alpha$. The value of a be 0.05/2 for two-sided 95% confidence interval. In the case where the examination is positive, FN and TN in formula (5) and (6) are replaced with TP and FP, respectively.

In order to calculate the disease onset risk after x months from the day of examination, first, the number of cases a(x), b(x), c(x), and d(x) in a period around x months after the examination are obtained. Furthermore, for a future risk prediction in the disease onset risk, for example, x1=1, x2=2, x3=3, . . . , x24=24 are used as specific values of x, corresponding to 24 periods from after one month to after 24 months. Even if a huge number of the cases of the past examination may be acquired, it would not necessarily that all period of examination be exactly arranged after the elapse of x months from the examination date. Therefore, a model of function $c(x)=f(x, \vec{a}, \vec{\theta})$ will be applied for a(x), b(x), c(x), and d(x). Here, the arrow superscript expresses a vector. A vector $\vec{a}$ is consisting of parameters for determining the form of a function f. By calculating values of $\vec{a}$ in advance, parameters in $\vec{a}$ can be read from a storage of prediction model data, and the function value of f can be calculated for elapsed months x. $\vec{\theta}$ expresses a vector, and indicates a value of a risk factor.

As a simple form of $f(x, \vec{a}, \vec{\theta})$, there is a linear function $f(x, \vec{a}, \vec{\theta})=(x, \vec{\theta}, 1)\cdot \vec{a}$ ("·" expresses an inner product of the vector). However, it is appropriate to be configured with a statistical model such as a Gail model.

$F(x, \vec{a}, \vec{\theta})$ is a value that relies not only on the number of elapsed months x from the examination date, but also relies on other risk factors. By substituting x into the equation of c(x) that is calculated in the above manner, the value of c can be calculated, and the predicted positive rate and the confidence interval can be calculated in the manner of equation (1) to equation (6).

By the prediction function 103, after the 24 points in time are obtained for a(x), b(x), c(x), and d(x), the processing circuitry 10 calculates the predicted positive rate and the confidence interval for each of the following x's. That is, the expected values of the predicted positive rate at 24 points in time will be calculated by $P_{ex}(x_1)$ to $P_{ex}(x_{24})$, respectively. Similarly, the upper limit value of the confidence interval of the predicted positive rate at the 24 points in time will be calculated by $P_{upper}(x_1)$ to $P_{upper}(x_{24})$, and the lower limit value of the confidence interval of the predicted positive rate at the 24 points in time will be calculated by $P_{lower}(x_1)$ to $P_{lower}(x_{24})$.

In step S205, by the prediction function 103, the processing circuitry 10 determines a recommended period and a non-recommended period until the next examination. A reference value for determining the recommended period is a standard value and a reference upper limit value of the risk prediction value. Specifically, for example, the risk prediction value is set so that the reference upper limit value is "0.1" and the standard value is "0.05". It should be noted that the reference upper limit value and the standard value are not limited to predetermined values, and can be changed on the screen.

For example, the recommended period for the next examination should be a period prior to a point in time at which the confidence interval upper limit value of the predicted positive rate and the standard value of the risk prediction value coincide. On the other hand, the non-recommended period for the next examination should be a period after the point in time at which the confidence interval upper limit value of the predicted positive rate and the standard value of the risk prediction value coincide.

It should be noted that although the present embodiment explains an example of a recommended period and a non-recommended period in relation to the next examination, it is not limited to an examination, and may also be related to other medical procedures such as surgery or therapy. That is, the recommended period may be a recommended period for the next medical procedure.

In step S206, by the presenting function 105, the processing circuitry 10 displays a graph including at least time course of the risk prediction and the recommended period until the next examination. The recommended period presentation processing is thus ended.

A display example of the recommended period according to the first embodiment will now be described with reference to FIG. 3.

Figure 3:
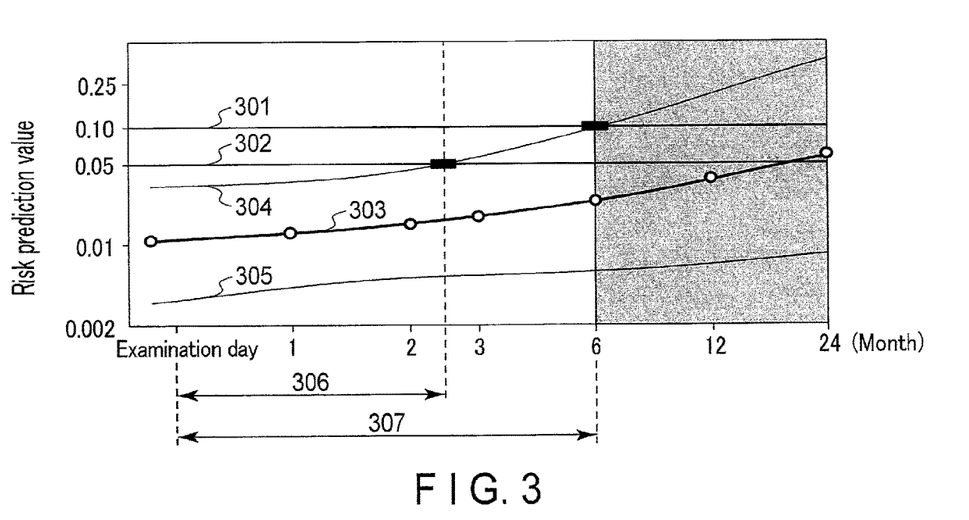
FIG. 3 is a diagram showing an example of presentation of a recommended period according to the first embodiment.

FIG. 3 is a graph showing the recommended period from the examination day to the next examination and an upper limit recommended period. The upper limit recommended period is a maximum upper limit period of the recommended period, in which the recommended period has elapsed and the risk of developing a disease will increase if the next examination is extended further. In the graph of FIG. 3, the vertical axis indicates a risk prediction value, and the horizontal axis indicates an elapsed period from the examination day. The values of the vertical axis and the horizontal axis of the graph may be switched and displayed. That is, the vertical axis may be the elapsed period from the examination day, and the horizontal axis may be the risk prediction value. A reference upper limit value 301 of a risk reference is set as "0.10" of the risk prediction value, and a standard value 302 of the risk reference is set as "0.05" of the risk prediction value.

A curve shown as a bold line indicates an expected value 303 of the predicted positive rate. A curve shown as a thin line above the expected value 303 indicates an upper limit value 304 of the confidence interval of the predicted positive rate, and a curve shown as a thin line below the expected value 303 indicates a lower limit value 305 of the confidence interval of the predicted positive rate. The expected value 303, the upper limit value 304, and the lower limit value 305 are all curves related to the disease onset risk. Since it may be considered that the upper limit of the disease onset risk should at least be considered, the upper limit value 304 should at least be displayed. The curve of the expected value and the curve of the lower limit of the confidence interval of the predicted positive rate do not have to be displayed.

As a setting method of the recommended period for the next examination, for example, in the case of determining a recommended period 306 of the next examination by the upper limit value 304 of the confidence interval of the predicted positive rate, a period from a day corresponding to the examination day to a point in time of an intersection point $P_{upper}(x_s)$ between the upper limit value 304 of the confidence interval and the standard value 302 of the risk reference is set as the recommended period 306. Here, $x_s$ is the number of months at which the upper limit value 304 coincides with the standard value 302 of the risk reference. As an upper limit recommended period 307, a period from a day corresponding to the examination day to a point in time of an intersection point $P_{upper}(x_u)$ between the upper limit value 304 of the confidence interval and the reference upper limit value 301 of the risk reference is set. Here, $x_u$ is the number of months at which the upper limit value 304 coincides with the reference upper limit value 301 of the risk reference.

On the other hand, in the case of determining the recommended period for the next examination by the expected value 303 of the predicted positive rate, the recommended period 306 will be set as a period from a day corresponding to the examination day to a point in time of an intersection point $P_{upper}(x_s)$ between the expected value 303 of the predicted positive rate and the standard value 302 of the risk reference. Here, $x_s$ is the number of months at which the expected value 303 coincides with the standard value 302 of the risk reference. Furthermore, as an upper limit recommended period $x_u$, a period from a day corresponding to the examination day to a point in time of an intersection point $P_{upper}(x_u)$ between the expected value 303 of the predicted positive rate and the reference upper limit value 301 of the risk reference is set. Here, $x_u$ is the number of months at which the expected value 303 coincides with the reference upper limit value 301 of the risk reference.

In the example of FIG. 3, the recommended period 306 based on the intersection point between the upper limit value 304 of the confidence interval and the standard value 302 of the risk reference is "2.5 months", and the upper limit recommended period 307 which is the intersection point between the upper limit value 304 of the confidence interval and the reference upper limit value 301 of the risk reference is "six months". It should be noted that the expected value 303 of the predicted positive rate, the upper limit value 304 of the confidence interval, the recommended period 306, and the upper limit recommended period 307 based on the examination day may be displayed at the top of the graph by numeric values.

Furthermore, by displaying the recommended period 306 and the upper limit recommended period 307 on the graph of FIG. 3, a period after the upper limit recommended period 307 will be presented as a non-recommended period which, in contrast to the recommended period, is too late for performing an examination. Thus, the user is able to recognize both the recommended period and the non-recommended period. It should be noted that the processing circuitry 10 may also emphasize and display the recommended period or the non-recommended period by the presenting function 105.

In the first embodiment, an example of generating the risk prediction value based on a two-by-two contingency table is presented. However, even in the case of performing the classification into two or more classes, such as into six classes, the predicted positive rate and the confidence interval can be calculated in the same manner. Specifically, based on a six-by-six contingency table, the predicted positive rate and the confidence interval should be calculated in the same manner as the two-by-two contingency table.

A more generalized example will be described. In the case of classifying and presenting the examination results into L classes (L is a positive number equal to or larger than three), the contingency table will be configured of L lines and two rows. In the L lines, items based on which the examination results are classified into L classes are arranged, and, in the two rows, items indicating the presence/absence of the disease are arranged.

The elements of v lines and j rows of the contingency table will be expressed by $f_{vj}(x, \vec{a}_{vj}, \theta)$. Therefore, the data of the prediction model is only $\vec{a}_{vj}$. In the case of expressing the examination result as L classes, as a determination method of the prediction model data $\vec{a}_{vj}$, a function fitting may be performed for adjusting $\vec{a}_{vj}$ so that the function $f_{vj}(x, \vec{a}_{vj}, \theta)$ is approximated to a probability distribution obtained from k pieces of past examination data, diagnosis data, and risk data. The function fitting can be implemented by various methods that are publicly known. For example, the data of the prediction model may be determined by performing the function fitting by adopting methods that are generally used, such as regression analysis, a linear optimization algorithm, a non-linear optimization algorithm, an artificial neural network, a random tree, and a support vector machine.

Furthermore, even in a case where the examination results are not binarized or multivalued classifications, but are a plurality of actual values, the predicted positive rate and the confidence interval can be calculated by expressing the distributions of a benign group and a malignant group by a model. For example, in the case of expressing a distribution of a negative group and a distribution of a positive group by a normal distribution model, an average value of the benign group, a standard deviation, the number of examinations, an average value of a malignant group, a standard deviation, and the number of examinations are calculated from the prediction model and the risk data, and a equation of a density function of a normal distribution is calculated for the negative group and the positive group, respectively. A plurality of actual values (vectors) obtained from the examination result data are substituted into the calculated density function equation. Probability densities of the distributions of the benign group and the malignant group close to the vectors are integrated, and the result thereof is multiplied by the number of malignant examinations and the number of benign examinations. From this result, it is possible to obtain a(x), b(x), c(x), and d(x), and the predicted positive rate and the confidence interval.

Specifically, in the case of expressing the examination result as M (M is a positive number) actual values, as an example, a case of expressing the distributions of the examination results of the negative group and the positive group as an M-dimensional normal distribution will be described. It should be noted that, other than the normal distribution, in the case of using a more complex distribution such as a Gaussian mixture model, the distribution parameters may differ. However, the predicted positive rate and the confidence interval can be obtained by the same procedure.

An M-dimensional probability density function of the negative group is expressed as $f_0(\vec{v}; x, \vec{a}_0, \theta, \vec{f}_0, R_0)$, and an M-dimensional probability density function of the positive group is expressed as $f_1(\vec{v}; x, \vec{a}_1, \theta, \vec{f}_1, R_1)$.

Here, since the distribution of the examination result is assumed to be a normal distribution, $\vec{f}_0$ indicates an average value of the examination data of the negative group, and $R_0$ indicates a covariance matrix of the examination data of the negative group. Furthermore, $\vec{f}_1$ indicates an average value of the examination data of the positive group, and $R_1$ indicates a covariance matrix of the examination data of the positive group. $\vec{A}_0$ and $\vec{a}_1$ are parameters for determining a function form. As the simplest form, a case in which the average and the covariance matrix do not depend on time x is assumed; however, they may also depend on time x. In the case of expressing the examination result as L classes, $f_0(\vec{v}; x, \vec{a}_0, \theta, \vec{f}_0, R_0)$ and $f_1(\vec{v}; x, \vec{a}_1, \theta, \vec{f}_1, R_1)$ correspond to an L line two-row contingency table fvj(x, $\vec{a}$vj, $\theta$).

Therefore, data relating to $\vec{f}_0, R_0, \vec{f}_1, R_1, \vec{a}_0$, and $\vec{a}_1$ may be used as the prediction model.

Furthermore, in the case of expressing the examination result as M actual values, as a determination method of data $\vec{f}_0, R_0, \vec{f}_1, R_1, \vec{a}_0$, and $\vec{a}_1$ of the prediction model, a function fitting may be performed for adjusting $\vec{f}_0, R_0, \vec{f}_1, R_1, \vec{a}_0$, and $\vec{a}_1$, so as to approximate the functions $f_0(\vec{v}; x, \vec{a}_0, \theta, \vec{f}_0, R_0)$ and $f_1(\vec{v}; x, \vec{a}_1, \theta, \vec{f}_1, R_1)$ to a probability distribution obtained from the past k pieces of examination data, diagnosis data, and risk data.

According to the first embodiment described above, assuming a case in which the same examination is repeatedly implemented to screen, etc. patients with a high risk of cancer, risk prediction is performed based on the current examination (the latest examination), from the risk factors and the examination results of the patient, and the recommended period, the upper limit recommended period, and the non-recommended period for the next examination are presented. Hypothetically, in the case where an examination is performed at a non-recommended period beyond the upper limit recommended period, the disease onset risk would exceed the upper limit value of the risk reference, elongating the period from the occurrence of the disease to the discovery thereof by the examination, which may miss the chance to detect and treat the disease at an early stage. Furthermore, since the upper limit value of the recommended period and the risk prediction value are displayed in one graph, the disease onset risk and the relationship to the examination interval can be easily grasped, allowing an appropriate examination interval or examination period to be presented for the next examination, thereby, presenting an appropriate recommended examination timing.

Second Embodiment

In the second embodiment, in addition to presenting a risk prediction value of a disease onset risk, a risk prediction value of a progression risk is calculated in a time series. The progression risk according to the present embodiment is a risk related to a progression rate of a disease that is diagnosed as malignant in a current examination progressing to an extent that would adversely affect treatment results. For example, a risk relating to a tumor that is diagnosed as malignant reaching a stage at which the size of the tumor would grow to 20 mm or larger is used. The progression risk may be calculated by the same method as calculating the disease onset risk.

It should be noted that, in the case of the progression risk, instead of the predicted positive rate in relation to a usual disease onset risk, a progression state predicted positive rate, which is based on the kind of progression state, is calculated. Furthermore, a prediction model relating to the progression risk is assumed to be prepared in advance in the same form as the disease onset risk.

Figure 4:
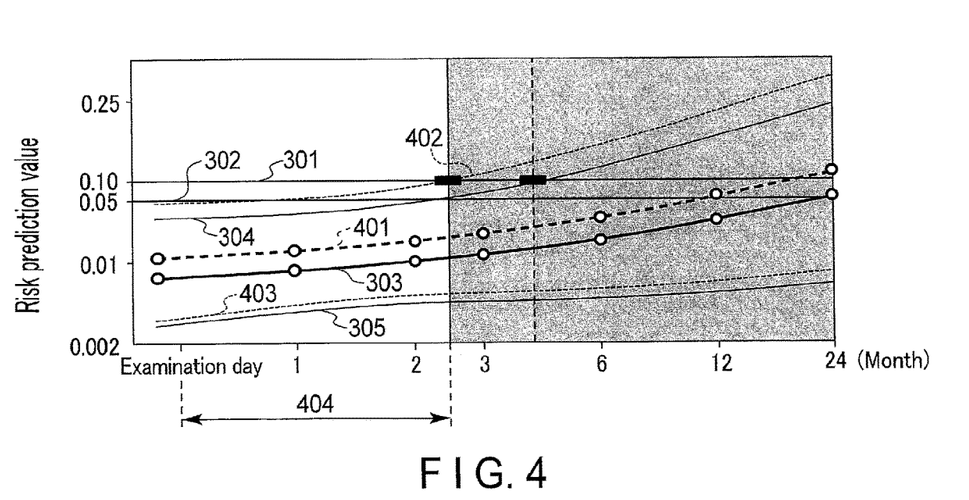
FIG. 4 is a diagram showing an example of presentation of a recommended period according to a second embodiment.

By a prediction function 103, processing circuitry 10 calculates each expected value of the progression state predicted positive rate using $Q_{ex}(x_0)$ to $Q_{ex}(x_{24})$ based on the prediction model in relation to the progression risk. Similarly, a confidence interval upper limit value of the progression state predicted positive rate of a current point in time and 24 points in time is calculated using $Q_{upper}(x_0)$ to $Q_{upper}(x_{24})$, and a confidence interval lower limit value of the progression state predicted positive rate of the current point in time and 24 points in time is calculated using $Q_{lower}(x_0)$ to $Q_{lower}(x_{24})$, respectively.

It should be noted that prediction model data relating to the progression risk can be generated more stably if there is examination data relative to 20 mm, such as examination data at a point in time where a tumor size does not exceed 20 mm, and examination data at a point in time where the tumor size exceeds 20 mm. However, since such examination data relative to 20 mm may not always be acquired even if a plurality of pieces of medical data are acquired, two pieces of examination data that are below and over 20 mm may be generated by using extrapolation and interpolation.

An example of presentation of a recommended period according to the second embodiment will now be described with reference to FIG. 4.

FIG. 4 is a graph showing a recommended period from the examination day to the next examination and an upper limit recommended period in the same manner as FIG. 3.

An expected value 401 of the progression state predicted positive rate indicating the calculated progression risk and an upper limit value 402 and a lower limit value 403 of a confidence interval are displayed on a graph as time-series data in the same manner as the expected value 303 of the predicted positive rate indicating the disease onset risk and the upper limit value 304 and the lower limit value 305 of the confidence interval.

In the example of FIG. 4, a case in which the recommended period is determined by an upper limit value of the confidence interval of the predicted positive rate and the progression state predicted positive rate is assumed. An upper limit recommended period 404 based on the progression risk is a period from a day corresponding to an examination day to a point in time of an intersection point between a reference upper limit value 301 of a risk reference and the upper limit value 402 of the confidence interval of the progression state predicted positive rate, which is "2.5 months" in the example of FIG. 4. On the other hand, an upper limit recommended period based on the disease onset risk is a period from a day corresponding to an examination day to a point in time of an intersection point between the reference upper limit value 301 of the risk reference and the upper limit value 304 of the confidence interval of the predicted positive rate, which is "4.1 months" in the example of FIG. 4.

In the case of determining the recommended period by an expected value of the predicted positive rate, the recommended period may be determined by an intersection point between the expected value of the predicted positive rate (or the progression state predicted positive rate) and a standard value of the risk reference. Furthermore, when a diagnosis result shows that a tumor is benign, the processing circuitry 10 may delete the graph of the progression risk using a presenting function 105.

According to the second embodiment described above, the recommended period for the next examination or the next medical procedure is set by the prediction model of the disease progression state. Therefore, for example, even if it is unclear whether a tumor is benign or malignant, when assuming that there is a possibility that the tumor may progress, when the examination should be retaken by can be easily determined and presented to a patient who has developed some kind of tumor. That is, since the recommended period can be set by considering a timing at which the upper limit value of the confidence interval of the progression state predicted positive rate of the disease onset risk and the progression risk exceeds the reference value, an appropriate recommended examination timing can be presented.

Third Embodiment

The third embodiment is related to a case in which, based on criteria of worsening, etc., for example, a tumor cannot be observed to be growing even after a lapse of time from a current examination; therefore, it is considered that a lesion would not be observed even if an examination is immediately performed. Therefore, by presenting a non-recommended period, which is a period that is too early to perform the examination, a redundant examination can be avoided.

Figure 5:
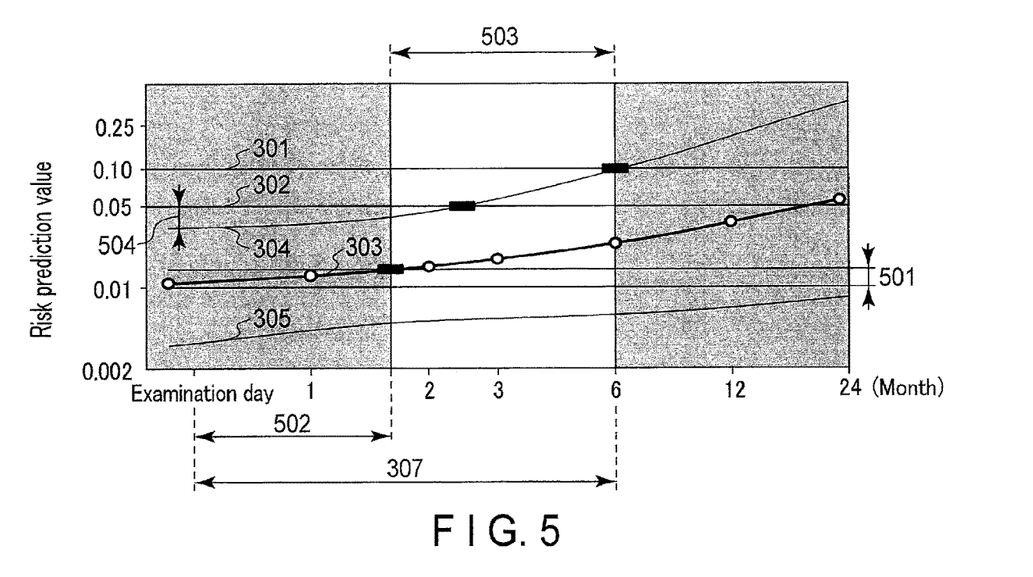
FIG. 5 is a diagram showing an example of presentation of a recommended period according to a third embodiment.

By a prediction function 103, the processing circuitry 10 sets the non-recommended period to a period from a day corresponding to the current examination to a point in time corresponding to a disease onset risk (a time course of an expected value or a time course of an upper limit value of a confidence interval) which has increased by a value equal to or higher than a predetermined value from a risk prediction value based on the current examination.

Furthermore, in another method, by the prediction function 103, the processing circuitry 10 sets the non-recommended period to a period from a day corresponding to the current examination to a point in time at which an increase rate of disease worsening coincides with a threshold value.

An example of presentation of a recommended period and a non-recommended period according to the third embodiment will be described with reference to FIG. 5.

In the graph of FIG. 5, a worsening reference rate 501 will be presented as a threshold value of determining the non-recommended period. The worsening reference rate 501 indicates an increased amount of a predetermined value from an expected value 303 of a predicted positive rate based on the current examination. If the expected value of the predicted positive rate increases beyond the worsening reference rate 501, the disease can be determined to be worsening. In the example of FIG. 5, a point in time corresponding to an intersection point between the worsening reference rate 501 and the expected value 303 of the predicted positive rate from the day corresponding to the examination day is presented, and a period from the day corresponding to the examination day to the above point in time is presented as a non-recommended period 502.

That is, even if an examination is performed during a period prior to the non-recommended period 502, since the increase amount is smaller than the worsening reference rate 501, there is a possibility that a change in the disease (tumor) cannot be detected even by re-examination. Therefore, a user can easily grasp the guide that is undesirable to perform the examination in the non-recommended period 502.

Furthermore, an upper limit recommended period 307 may be calculated by a method similar to that of the first embodiment. Therefore, a period between the non-recommended period 502 and the upper limit recommended period 307 becomes a recommended period 503.

It should be noted that, by the prediction function 103, the processing circuitry 10 may also calculate a period from the day corresponding to the examination day to a point in time at which a difference between the standard value 302 of the risk reference and the expected value 303 becomes a predetermined value as the non-recommended period 502.

Furthermore, for a more careful determination, in the case of assuming the worst case, as shown in FIG. 5, the non-recommended period 502 may be calculated as a period up to a point in time where a difference 504 between the standard value 302 of the risk reference and the upper limit value 304 of a confidence interval of the predicted positive rate becomes a predetermined value.

According to the third embodiment described above, by calculating the non-recommended period, which is a period in which it is too early to perform the examination, a redundant examination can be avoided. This is because, in a period prior to a lower limit recommended period, which is a period not long after the current examination, the disease may not be assumed to be progressing in consideration of the risk prediction value. Therefore, an examination performed prior to the lower limit recommended period may be redundant. Since such a redundant examination can be avoided, there is a merit for both the patient and the hospital.

Fourth Embodiment

In the case of performing an examination that is accompanied by exposure, such as the case of X-ray CT imaging, if the examination is performed a plurality of times in short intervals, an additional disease risk, which is a risk of developing other diseases caused by exposure, may increase. Therefore, in addition to the recommended period presented in the above-described embodiment, an additional disease risk may be presented. Accordingly, a non-recommended period based on the additional disease risk and a recommended period in which the additional disease risk is considered can be presented.

Figure 6:
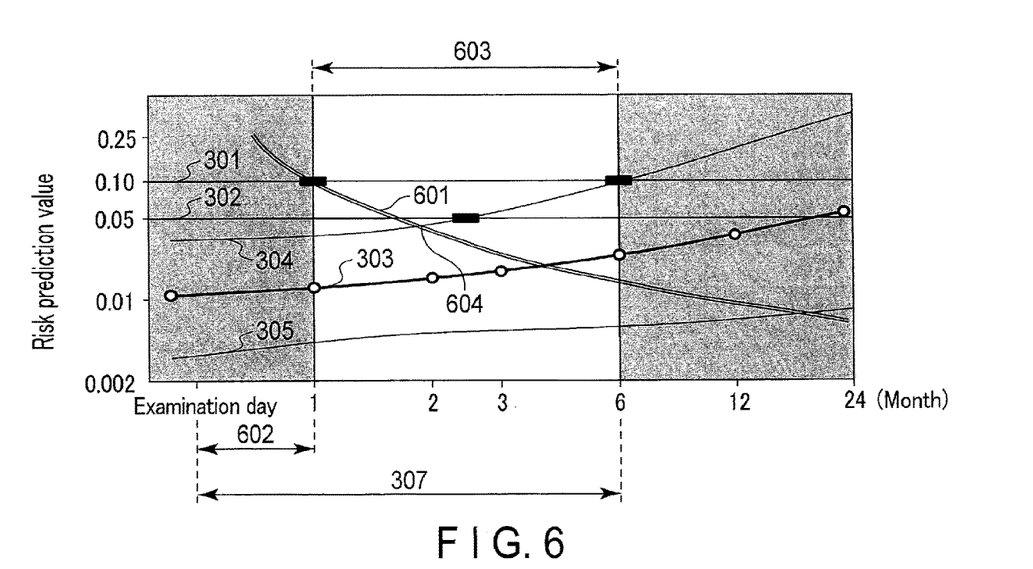
FIG. 6 is a diagram showing an example of presentation of a recommended period according to a fourth embodiment.

A prediction model of an additional disease risk which occurs due to exposure with the passage of time may be calculated by, for example, a prediction function 103 of processing circuitry 10 using a general calculation method based on statistical data. The processing circuitry may also acquire a prediction model of an additional disease risk that is calculated in advance from outside.

An example of presentation of a recommended period according to the fourth embodiment is described with reference to FIG. 6.

FIG. 6 is a graph in which a transition graph 601 of the additional disease risk is displayed on the graph shown in FIG. 3 in a time series.

A period from a day corresponding to an examination day to a point in time of an intersection point between the transition graph 601 of the additional disease risk and a reference upper limit value 301 of a risk reference is presented as a non-recommended period 602. It should be noted that the non-recommended period 602 may be presented by using a point in time of an intersection point between the transition graph 601 and a standard value 302 of the risk reference. Therefore, a recommended period 603 between the non-recommended period 602 and an upper limit recommended period 307 can be presented, and a user can easily grasp the recommended period 603.

It should be noted that the transition graph 601 of the additional disease risk and an expected value 303 of a predicted positive rate may be combined to display a total value of a disease risk of a lesion. Alternatively, a graph may be generated in which a larger risk prediction value between the transition graph 601 of the additional disease risk and the expected value 303 of the predicted positive rate is adopted for each date. Specifically, in the graph of the total value in the example of FIG. 6, a period from the examination day to an intersection point 604 is shown in the transition graph 601 of the additional disease risk, and a period after the intersection point 604 becomes the expected value 303 of the predicted positive rate.

According to the fourth embodiment described above, the recommended period and the non-recommended period for the next examination can be presented based on the additional disease risk caused by arranging an examination, such as due to exposure caused by an examination; thereby, an appropriate recommended examination timing can be presented.

Fifth Embodiment

In the fifth embodiment, each disease onset risk is calculated based on a prediction model in relation to each of a plurality of diseases, and the disease onset risks are displayed together.

An example of presentation of a recommended period according to the fifth embodiment is described with reference to FIG. 7.

Figure 7:
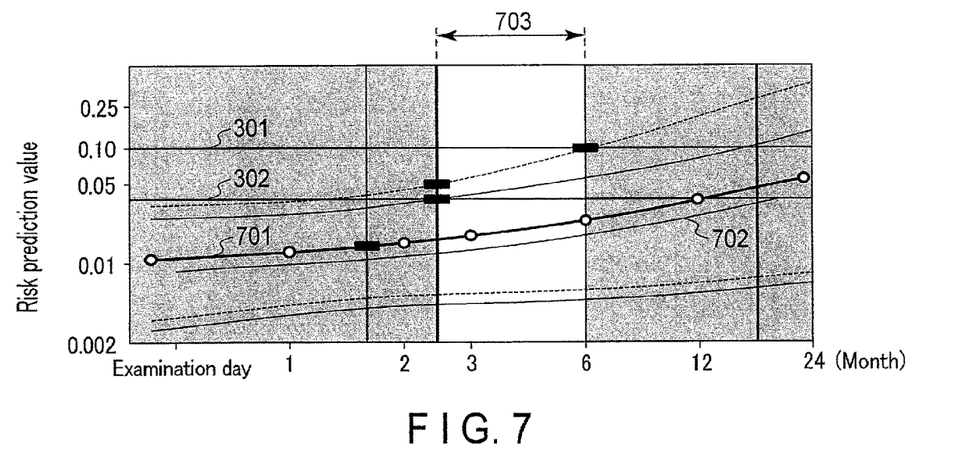
FIG. 7 is a diagram showing an example of presentation of a recommended period according to a fifth embodiment.

In FIG. 7, a transition graph (an expected value and a confidence interval of a predicted positive rate) of a disease onset risk of each of a plurality of diseases is displayed. As an example of the transition graph, an expected value 701 of a predicted positive rate of lung cancer and an expected value 702 of a predicted positive rate of pulmonary emphysema are displayed.

Here, by a presenting function 105, the processing circuitry 10 may present an overlapping region between a recommended period based on a prediction model of lung cancer and a recommended period based on a prediction model of pulmonary emphysema as a comprehensive recommended period. By presenting the comprehensive recommended period, a recommended period for a next examination in the case of assuming a plurality of diseases can be presented.

The processing circuitry 10 may adopt a latest period among a plurality of non-recommended periods for a lower limit of the comprehensive recommended period, and an earliest period among a plurality of upper limit recommended periods for an upper limit of the comprehensive recommended period. In FIG. 7, as a comprehensive recommended period 703, a lower limit recommended period based on the prediction model of pulmonary emphysema, which is a later period, is adopted for a lower limit, and an upper limit recommended period based on the prediction model of lung cancer, which is an earlier period, is adopted for an upper limit.

It should be noted that a prediction model for each metastatic pattern of cancer may be presented instead of a prediction model based on each of a plurality of diseases. For example, a recommended period in the case where lung cancer has metastasized to a lymph node may be presented. The calculation methods of the recommended period and the overlapping region, etc. are the same as in the case of calculations based on a plurality of diseases.

Furthermore, each of the prediction models for each disease may be stored in association with an examination type for testing the disease. In the case of presenting the recommended period, an examination type associated with a prediction model may also be displayed.

Furthermore, in the case of performing a treatment in one prediction model, the kind of disease onset risk that may occur may also be branched and displayed. That is, in the case of performing a treatment, etc. at a certain point in time in the future, the disease onset risk may be considered to change.

Figure 8:
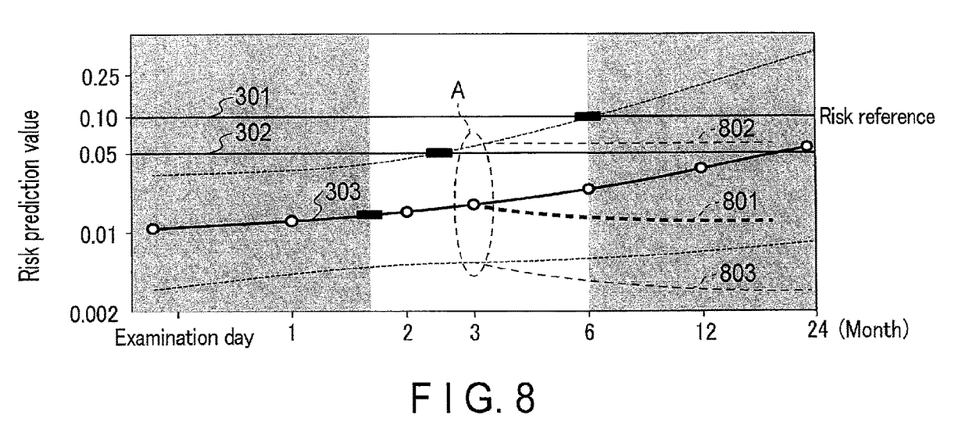
FIG. 8 is a diagram showing a modified example of an example of presentation of a disease onset risk.

An example of branching and presenting a graph of a disease onset risk at a certain point in time in the future is shown in FIG. 8.

As a reference for branching the graph of the disease onset risk, there is a case in which the reference is based on determining a disease type by a test performed at a point in time in the future which is to be a branching point, a case in which the reference is based on a lesion type changing at a point in time in the future which is to be a branching point, or a case in which the reference is based on starting a treatment at a point in time in the future which is to be a branching point.

The example of FIG. 8 is a case in which a treatment is assumed to be started from a branching point A. By the presenting function 105, the processing circuitry 10 branches an expected value 801 of a predicted positive rate and an upper limit value 802 and a lower limit value 803 of a confidence interval from an original graph at the branching point A, and presents them.

According to the fifth embodiment described above, by calculating respective disease onset risks based on a prediction model in relation to each of a plurality of diseases, and displaying them all together, information desired by a user can be collectively presented.

Sixth Embodiment

In the sixth embodiment, by clicking on a recommended period with a mouse, or by touching a region in which the recommended period is displayed in the case of a touch display, an examination reservation system is connected, and an examination reservation screen is displayed. In this manner, by referring to the examination reservation screen, unoccupied days and unoccupied hours can be searched for, and an examination can be reserved. This will improve workflow.

An example of examination reservation processing according to the sixth embodiment will be described with reference to FIG. 9.

Figure 9:
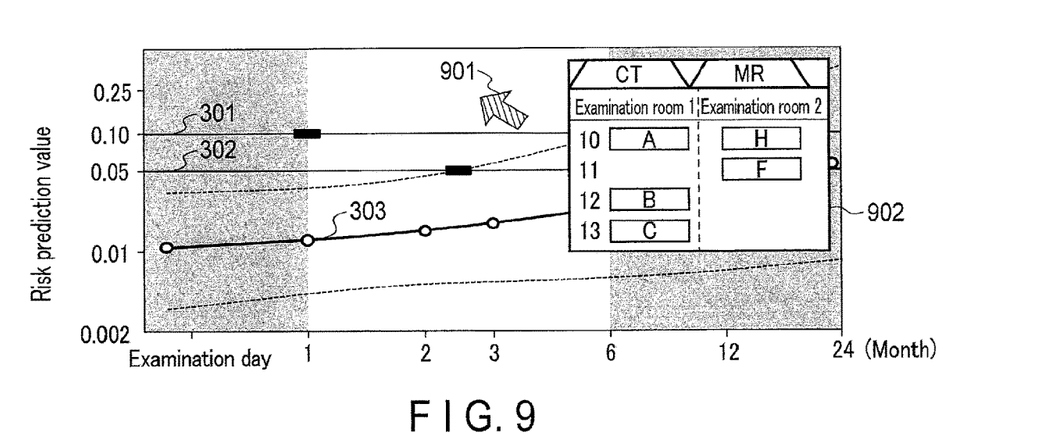
FIG. 9 is a diagram showing an example of examination reservation processing according to a sixth embodiment.

FIG. 9 shows an example of presentation in which the recommended period is displayed. Here, when a mouse cursor 901 is placed on the recommended period and clicked (or double clicked), for example, using a presenting function 105, processing circuitry 10 connects to the examination reservation system, and acquires and displays an examination reservation window 902 (also referred to as a reservation screen) on a screen.

On the examination reservation window 902, for example, an examination tab of each medical image diagnostic apparatus is displayed, and an examination schedule and a reservation list are displayed for each examination tab. Specifically, in the example of FIG. 9, a CT examination tab and an MR examination tab are displayed, and a time schedule is displayed in which a time slot and an examination room for which an examination reservation is made for a patient can be grasped at a glance. It should be noted that the examination reservation window 902 may be displayed in an overlapping manner on a graph display of for example a disease onset risk, or may be displayed in parallel with the graph. The examination reservation window 902 may also be displayed on another display.

In the case where a user of an electronic medical record system, such as a doctor, makes a reservation for an examination for a subject in the recommended period, the user clicks or drags an unoccupied time slot on the examination reservation window 902. The reservation is accepted by the processing circuitry 10 transmitting the time slot corresponding to the clicked or dragged portion and patient information of the subject for which prediction processing of the recommended period is executed to an electronic medical record to the examination reservation system. In this manner, the examination reservation of the subject can be completed.

In the sixth embodiment described above, by clicking a recommended period using a mouse, or by touching a region in which the recommended period is displayed in the case of a touch display, an examination reservation system can be connected, and an examination reservation window can be displayed. In this manner, a user can easily make examination reservations while viewing the recommended period.

Seventh Embodiment

The first to the sixth embodiments were described by assuming examples of executing risk prediction processing on an electronic medical record. However, a medical information processing apparatus for executing the risk prediction processing may be provided separately from the electronic medical record, and an operation of the electronic medical record and the risk prediction processing by the medical information processing apparatus may be executed in parallel. Alternatively, this may be executed alone by the medical information processing apparatus.

Figure 10:
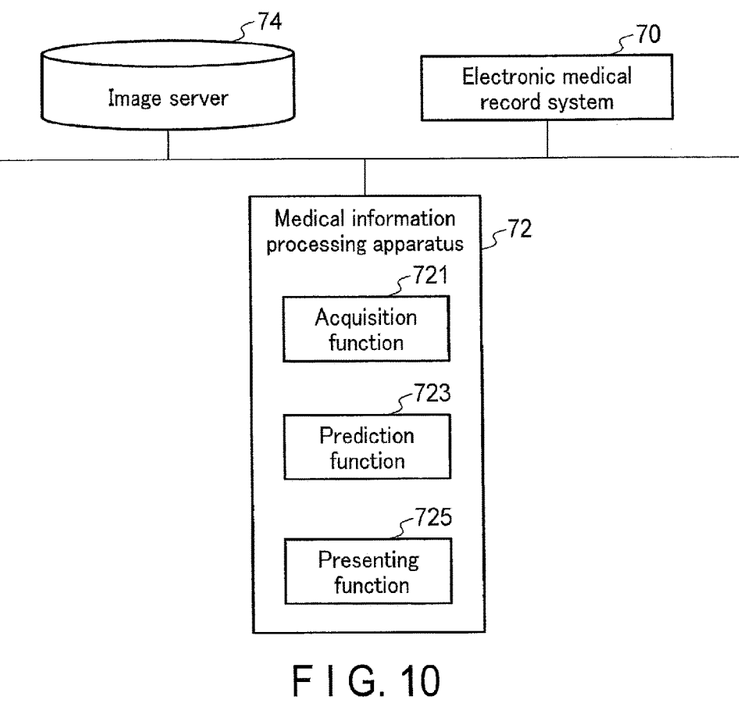
FIG. 10 is a block diagram showing a medical system including a medical information processing apparatus.

A medical system including a medical information processing apparatus according to the seventh embodiment will be explained with reference to the block diagram of FIG. 10.

The medical system includes an electronic medical record system 70, a medical information processing apparatus 72, and an image server 74.

The electronic medical record system 70 displays, for example, whether an examination result is positive or negative and a numeric value of the examination result.

The medical information processing apparatus 72 has the same configuration as that of the processing circuitry described in the first embodiment.

The image server 74 is a picture archiving and communication system (PACS) server, and stores an examination image of a subject, etc.

The medical information processing apparatus 72 performs recommended period presentation processing relating to the recommended period and the non-recommended period described in the first to the sixth embodiments, and transmits various pieces of data in a manner to be displayed by the electronic medical record system 70. It should be noted that the recommended period presentation processing may be executed by a user transmitting an instruction from the electronic medical record system 70 to the medical information processing apparatus 72, or by a user operating the medical information processing apparatus 72 and providing an instruction to execute the recommended period presentation processing to the medical information processing apparatus 72.

According to the seventh embodiment described above, regardless of whether or not the processing circuitry for executing the recommended period presentation processing is incorporated into the electronic medical record system, the recommended period presentation processing can be executed in the same manner as the first to the sixth embodiments. Furthermore, the medical information processing apparatus and the electronic medical record system can be provided separately and perform operations separately. Furthermore, the medical information processing apparatus may execute the recommended period presentation processing alone.

It should be noted that, although the first to the seventh embodiments described above show examples of displaying the recommended periods using graphs, instead of using graphs, the recommended periods may be displayed by numeric values, or may be displayed by using graphs and numeric values in combination. Furthermore, data relating to the recommended period and the non-recommended period may be transmitted to the electronic medical record systems 1 and 70 and an external terminal of the medical system.

According to the first to the seventh embodiments described above, an appropriate examination timing can be presented.

The functions of the processing circuitry 131 explained in the embodiment can be executed based on a software program. The functions of the processing circuitry 131 are stored in a magnetic disc (flexible disc, hard disc, etc.), an optical disc (CD-ROM, CD-R, CD-RW, DVD-ROM, DVD±R, DVD±RW, etc.), a semiconductor memory, or a similar storage medium, as a program executable by a computer.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. A medical information processing apparatus, comprising:
   processing circuitry configured to
      predict, based on subject information and a prediction model of a disease onset risk, a time course of the disease onset risk in relation to a subject; and
      calculate, based on the predicted time course of the disease onset risk, a recommended period appropriate for arranging a next examination or medical procedure, and present the calculated recommended period and at least one of a period earlier than the recommended period and determined to be too early for the next examination or medical procedure and a period later than the recommended period and determined to be too late for the next examination or medical procedure as a non-recommended period that is inappropriate for arranging the next examination or medical procedure, wherein the processing circuitry is further configured to receive, from a user, selection of the recommended period displayed on a display; and in response to receiving the selection, display an examination reservation window in which an examination reservation for the subject is made in the recommended period.

2. The medical information processing apparatus according to claim 1, wherein the processing circuitry is further configured to present period that is too early for the next examination or medical procedure as the non-recommended period.

3. The medical information processing apparatus according to claim 1, wherein the processing circuitry is further configured to present both the period that is too late for the next examination or medical procedure and the period that is too early for the next examination or medical procedure, so as to present two non-recommended periods and the recommended period.

4. The medical information processing apparatus according to claim 1, wherein the processing circuitry is further configured to present, as the non-recommended period, a period from a last examination or medical procedure to a point in time where a difference value coincides with a threshold value, the difference value indicating a difference between a risk prediction value corresponding to the predicted time course and a value set in accordance with a risk reference.

5. The medical information processing apparatus according to claim 1, wherein the processing circuitry is further configured to present the non-recommended period as a period from the last examination or medical procedure to a point in time where an increase rate of a disease worsening coincides with a threshold value.

6. The medical information processing apparatus according to claim 1, wherein the processing circuitry is further configured to present the non-recommended period as a period after a point in time where a risk prediction value corresponding to the predicted time course and a value set in accordance with a risk reference coincide.

7. The medical information processing apparatus according to claim 1, wherein the processing circuitry is further configured to predict, based on a prediction model of a progression risk in relation to a progression rate of a disease, a time course of the progression risk in relation to the subject, and present the predicted time course of the progression risk.

8. The medical information processing apparatus according to claim 1, wherein the processing circuitry is further configured to predict, based on a prediction model of an additional disease risk indicating a risk of developing a disease due to the examination or the medical procedure, a time course of the additional disease risk in relation to the subject, and present the predicted time course of the additional disease risk.

9. The medical information processing apparatus according to claim 1, wherein the processing circuitry is further configured to predict, based on a prediction model of each of a plurality of disease onset risks, a plurality of time courses of each of the plurality of disease onset risks in relation to the subject, and present the predicted plurality of time courses of each of the plurality of disease onset risks.

10. The medical information processing apparatus according to claim 9, wherein the processing circuitry is further configured to present, as a comprehensive recommended period, a region in which each transition period based on time courses of each of the plurality of disease onset risks overlaps.

11. The medical information processing apparatus according to claim 1, wherein when the recommended period is selected, the processing circuitry is further configured to present a reservation screen indicating a reservation list of examinations or medical procedures in the recommended period.

12. The medical information processing apparatus according to claim 1, wherein the processing circuitry is further configured to emphasize at least one of the recommended period or the non-recommended period in a graph in which a first axis indicates an elapsed period from a current point in time, and a second axis indicates the time course of the disease onset risk.

13. The medical information processing apparatus of claim 1, wherein the processing circuitry is further configured to display the recommended period, the non-recommended period, and a risk prediction curve corresponding to the predicted time course together on a same graph.

14. A medical information processing method, comprising:

predicting, based on subject information and a prediction model of a disease onset risk, a time course of the disease onset risk in relation to a subject; and calculating, based on the predicted time course of the disease onset risk, a recommended period appropriate for arranging a next examination or medical procedure, and presenting the recommended period and at least one of a period earlier than the recommended period and determined to be too early for the next examination or medical procedure and a period later than the recommended period and determined to be too late for the next examination or medical procedure as a non-recommended period that is inappropriate for arranging the next examination or medical procedure, wherein the method further comprises receiving, from a user, selection of the recommended period displayed on a display, and, in response to receiving the selection, displaying an examination reservation window in which an examination reservation for the subject is made in the recommended period.

15. An electronic medical record system, comprising:

a display;

reception circuitry configured to receive an instruction from a user;

prediction circuitry configured to predict, based on subject information and a prediction model of a disease onset risk, a time course of the disease onset risk in relation to a subject based on the instruction from the user; and presentation circuitry configured to present, based on the predicted time course of the disease onset risk, a recommended period appropriate for arranging a next examination or medical procedure, and present at least one of a period earlier than the recommended period and determined to be too early for the next examination or medical procedure and a period later than the recommended period and determined to be too late for the next examination or medical procedure as a non-recommended period that is inappropriate for arranging the next examination or medical procedure, wherein the presentation circuitry is further configured to receive, from a user, selection of the recommended period displayed on a display, and in response to receiving the selection, display an examination reservation window in which an examination reservation for the subject is made in the recommended period.

\* \* \* \* \*